United States Patent [19]

McCabe et al.

[11] Patent Number: 5,149,655

[45] Date of Patent: Sep. 22, 1992

[54] APPARATUS FOR GENETIC TRANSFORMATION

[75] Inventors: Dennis E. McCabe, Middleton; Brian J. Martinell, Madison, both of Wis.

[73] Assignee: Agracetus, Inc., Middleton, Wis.

[21] Appl. No.: 541,563

[22] Filed: Jun. 21, 1990

[51] Int. Cl.$^5$ .............................................. C12M 1/00
[52] U.S. Cl. ................................... 435/287; 435/172.1; 435/313; 935/52; 935/53; 935/85; 604/68
[58] Field of Search .......... 435/287, 173, 172.1–172.3, 435/313; 935/52, 53, 85; 604/68–70, 72, 140, 141, 146; 128/24 EL; 73/12, 167; 239/81

[56] References Cited

U.S. PATENT DOCUMENTS

| | | | |
|---|---|---|---|
| 3,942,531 | 3/1976 | Hoff et al. | 128/24 EL |
| 4,302,670 | 11/1981 | Zaderej | 250/324 |
| 4,715,376 | 12/1987 | Nowacki et al. | 128/24 EL |
| 4,879,993 | 11/1989 | Reichenberger et al. | 128/24 EL |
| 4,945,050 | 7/1990 | Sanford et al. | 435/172.1 |
| 5,015,580 | 5/1991 | Christou et al. | 435/172.1 |

FOREIGN PATENT DOCUMENTS

| | | |
|---|---|---|
| 0164575 | 5/1985 | European Pat. Off. |
| 0270356 | 6/1988 | European Pat. Off. |
| WO85/01856 | 5/1985 | PCT Int'l Appl. |

OTHER PUBLICATIONS

Klein et al., "Particle Gun Technology: A Novel Method for the Introduction of DNA into Living Cells," Poster #28, *Biotechnology in Plant Science: Relevance to Agriculture in the Eighties*, Jun. 23-27, 1985.

Sanford, "The Biolistic Process," *Tibtech*, 6:299–302 (1988).

Klein et al., "High–velocity Microprojectiles for Delivering Nucleic Acids into Living Cells," *Nature*, 327:70–73 (1987).

Moynahan et al., "Development of Jet Injection . . . ," *Brit. Med. Jour.*, 1541-1543 (1965).

LaChapelle et al., "Tatouages Permanents Consecutifs . . . ," *Ann. Dermatol. Venereol.* (Paris), 109:939-946 (1982).

Johnston, "Biolistic Transformation: microbes to mice," *Nature*, 346:776-777 (1990).

Negrutiu, *Biotechnology and Ecology of Pollen*, (Conference) (1985).

Sanford et al., "Delivery of Substances into Cells and Tissues Using a Particle Bombardment Process," *Particulate Science and Technology*, 5:1:pp. 27-37 (1987).

Hepher, "Microinjection of DNA . . . ," *Genetic Engineering of Plants and Microorganisms Important for Agriculture*, pp. 32-33 (1985).

Flavell, "Prospects for Transforming Monocot Crop Plants," *Nature*, 307:108-109 (1984).

Korohoda, "High Efficiency Genetic Transformation in Maize Induced by Exogenous DNA," *A. Pflanzenphysiol. Bd.*, 94:95-99 (1979).

Ohta, "High-efficiency Genetic Transformation of Maize by a Mixture of Pollen and Exogenous DNA," *Proc. Natl. Acad. Sci.*, 83:715-719 (1986).

Graves et al., "The Transformation of *Zea mays* Seedlings with *Agrobacterium tumefaciens*," *Plant Mol. Biol.*, 7:43-50 (1986).

*Primary Examiner*—Robert J. Warden
*Assistant Examiner*—William H. Beisner
*Attorney, Agent, or Firm*—Quarles & Brady

[57] ABSTRACT

An apparatus for the particle mediated genetic transformation of organisms in vivo has two parts, a support unit and a hand unit. The hand unit is of a convenient hand manipulable size so that it can be placed readily against the organism the cells of which are to be transformed. The hand unit is connected to the support unit by a flexible umbilical so that the hand unit can be placed where desired. The apparatus is particularly well adapted for the convenient transformation of somatic cells of whole animals or humans.

10 Claims, 4 Drawing Sheets

APPARATUS FOR GENETIC TRANSFORMATION

The present invention relates to the general field of genetic engineering of organisms and relates, in particular, to a convenient and easy to use apparatus for the insertion of foreign genetic material into the tissues of living organisms.

BACKGROUND OF THE INVENTION

There is much interest in the general field of the genetic engineering of living organisms. In the genetic engineering of an organism, foreign genetic material, typically a DNA vector constructed so as to express a suitable gene product in the cells of the target organism, is transferred into the genetic material of cells of the organism, through one of a variety of processes. In the past, the transformation techniques have varied widely from organism to organism, and few genetic transformation techniques have been developed which seem applicable to a large number of different organisms in different biological classes or kingdoms. Some of the prior art mechanisms utilized for the insertion of genetic material into living tissues include: direct micro-injection, electroporation, a technique in which individual cells are subjected to an electric shock to cause those cells to update DNA from a surrounding fluid; liposome-mediated transformations, in which DNA or other genetic material is encapsulated in bilipid vesicles which have an affinity to the cell walls of target organisms; and certain specific types of biological vectors or carriers which have the ability to transfect genetic material carried within them into certain specific target organisms, such as the plant transformation vector *Agrobacterium tumefaciens* and retroviral vectors which are used in animal hosts.

One technique exists which, in theory, seems applicable to a large range of host organisms. This theory is referred to as particle-mediated genetic transformation. In this technique, the genetic material, be it RNA or DNA, is coated on the small carrier particles. The carrier particles are then physically accelerated into the tissue which is to be transformed. For the process to work, the carrier particles are selected to be small enough so that they may be hurled through the walls and into the interior of cells of the target organism, without causing injury or significant harm to those cells. Several articles have been published describing the techniques and the apparatus utilized in such a particle-mediated transformation technique. Klein et al. "High-Velocity Microprojectiles for Delivering Nucleic Acids into Living Cells," *Nature*, 327:70-73 (1987); and Sanford, "The Biolistic Process," *TIB - TECH*, 6:299-302 (1988). Sanford and Klein, who are early investigators investigating particle-mediated transformation techniques, utilized a macro-particle to accelerate the small carrier or microparticles. The macroprojectile or macro-particle used by Sanford and Wolfe was literally a bullet fired by a ballistic shell which was, in actual fact, a firearm shell. The use of such extremely high velocity acceleration techniques required a large instrument, with very good shielding and safety interlocks, to prevent inadvertent harm to the experimenters.

A second technique developed for the acceleration of carrier particles carrying biological molecules into target cells for genetic transformations was based on a shock wave created by a high voltage electric spark discharge. This apparatus is described in European published patent applications numbers 270,356 and 301,749. The apparatus described in those published applications involves a pair of spaced electrodes placed in a spark discharge chamber. A high voltage electric discharge is then passed between the electrodes to vaporize a droplet of water placed between the electrodes. The spark discharge vaporizes the water droplet creating a pressure wave, which accelerates a carrier sheet previously placed on the discharge chamber. The carrier sheet carries thereon the carrier particles, which have the biological genetic materials thereon. The carrier sheet is accelerated toward a retainer where the carrier sheet is stopped, the particles are separated from it, and only the carrier particles pass on into the biological tissues. The design for the particle acceleration apparatus as described in these European publications was one which involved a desk top, or bench top, apparatus of relatively significant size and complexity and which was relatively immobile.

SUMMARY OF THE INVENTION

The present invention is summarized in that particle acceleration apparatus is described in which the operative portion of the device is hand held, so that it may be utilized for the acceleration of particles carrying biological molecules into larger whole organisms which cannot readily be placed on a bench top unit.

It is a object of the present invention to provide a hand-held particle acceleration apparatus so that genetic transformations can be accomplished more readily and with greater facility for larger organisms and for biological systems in vivo.

It is an object of the present invention further to provide such a hand held particle acceleration device in which the cartridge carrying the carrier particles can be readily replaced with great facility so that repetitive particle acceleration procedures can be performed in the field with minimal manipulation of the instrument.

Other objects, advantages, and features of the present invention will become apparent from the following specification when taken in conjunction with the accompanying drawings.

Brief Description of the Drawings

FIG. 5 is a schematic illustration of the electrical circuitry necessary to power the instrument of FIG. 1.

Description of the Preferred Embodiment

Figure 1:
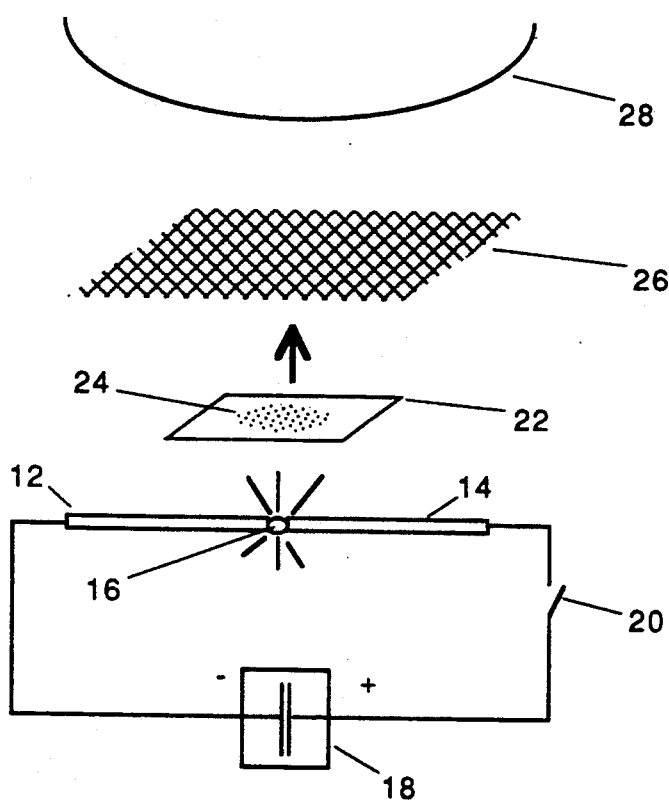
FIG. 1 is a schematic illustration of the particle acceleration device constructed in accordance with the present invention as utilized to perform a somatic cell genetic transformation on a mammal.

Illustrated in FIG. 1 is a schematic illustration intended to illustrate the general method of operation of a particle acceleration genetic transformation device operating on the principal of the preferred embodiment here. As shown in FIG. 1, a pair of electrodes 12 and 14 are provided spaced apart with a spark gap distance between them. The spark gap distance is bridged by a drop of water 16. The end of each of the electrodes 12 and 14 is connected to one terminal of a high voltage capacitor 18, with one of the terminals being connected through a switch 20. After the capacitor 18 is charged and when the switch 20 is closed, high voltage electrical energy is transferred from the capacitor 18 to create a potential between the electrodes 12 and 14. If the potential is sufficiently high, in the order of several kilovolts, a spark will bridge the gap between the electrodes 12 and 14. The electrical spark bridging the electrodes 12 and 14 instantly vaporizes the water vapor droplets 16. The expanding shock wave created by the instant vaporization of the water droplet 16 propagates radially outward in all directions. Previously placed within the zone which is affected by the shockwave is a carrier sheet 22. The carrier sheet 22 has previously been coated with a number of tiny carrier particles 24. The carrier particles 24 are of very dense material, preferably a metal such as gold, and are of an extremely small size, on the order of a fraction to a few microns in size. The carrier particles 24 are of dense material so that they will readily retain momentum and are sufficiently small sized so that they are small in relation to the cells of the organism which they are intended to transform. It has been found that carrier particles of a size of a few microns can enter living cells, by penetrating the cell walls thereof, without unduly adversely affecting the ability of most of the living cells to survive. In other words, the carrier particles can enter living cells without killing them. The carrier particles in an apparatus such as that shown in FIG. 1 are also coated. The carrier particles 24 are coated with a genetic construct, typically DNA or RNA, which is intended to be inserted into the living cells of the target organism.

In the general scheme of the apparatus of FIG. 1, the carrier sheet 22 is propelled upward by the expanding shock wave from the vaporization of the water droplets 16. The carrier sheet travels upward until it impacts a retaining screen 26 which, as its name implies, is simply a rigid metallic screen intended to retain the carrier sheet 22. When the carrier sheet 22 hits the retaining screen 26, it stops. However, the momentum of movement of the carrier sheet 22, with the carrier particles 24 thereon, is retained by the carrier particles 24, and the carrier particles 24 therefore fly upward from the retaining sheet 26 into the target organism 28. The target organism is the biological organism, tissue or cell culture into which it is desired to transfer the genetic material coated onto the carrier particles 24.

It has been previously found that an electric spark discharge transformation apparatus, operating in accordance with the methodology of FIG. 1, has been capable of achieving both somatic cell and germ line transformation of a variety of living organisms from a variety of classes in both the plant and animal kingdoms. For example, published European patent application No. 270356 discloses an earlier version of an apparatus operating on this principal which was utilized to transform pollen of corn plants. European published application No. 301,749 discloses an improved electric spark discharge transformation apparatus, and a method for transforming a meristematic or embryonic tissues of soybean. The latter, second generation, apparatus has also been successfully applied to the transformation of woody plant species, plant and animal cells in culture, callus cultures of a wide variety of plants, and animal tissues, both intact (i.e. in vivo) and dissected tissues, and both somatic and germ line cells.

In further developing the technology of particle-mediated transformation of cells, one of the areas of inquiry has been toward the somatic transformation of various cell types of larger organisms, such as intact plants or animals. The particle-mediated transformation apparatus disclosed in the above European applications may be used for large organisms, but is not convenient, due to the fact that it is fixed in character. It is sometimes difficult to maneuver a large organism, be it plant or animal, into a location at which it can be transformed by a fixed particle acceleration device. Accordingly, the present invention is intended to deal with such large organisms on the theory that if the organism cannot come to the transformation device, the transformation device can go to the organism.

Figure 2:
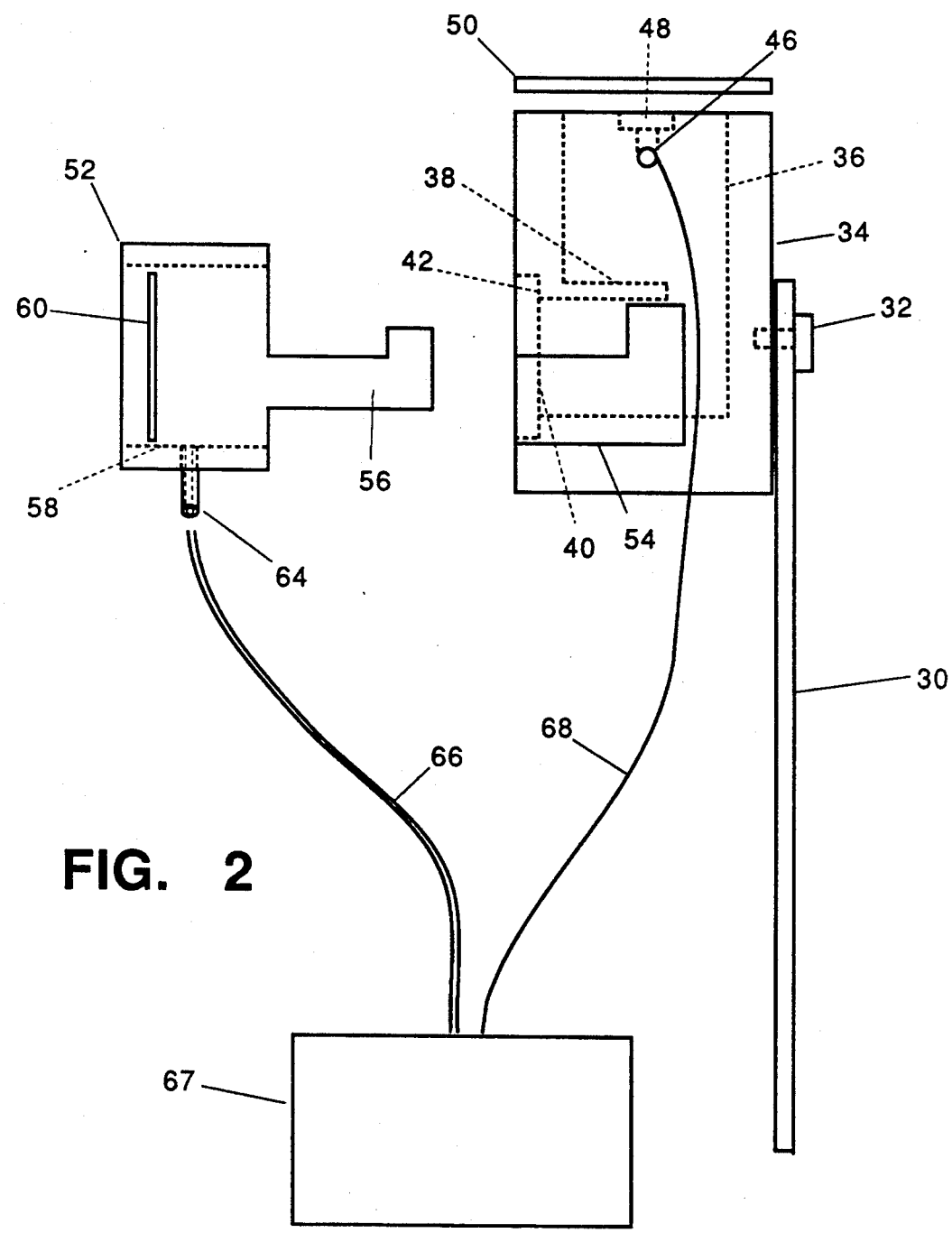
FIG. 2 is a front plan view of the particle acceleration device of FIG. 1 with the retaining insert removed.

Illustrated in FIG. 2 is a side elevation view of a two part hand-manipulable particle acceleration device constructed in accordance with the present invention. This device is one which is portable and hand manipulable, so that it may be readily and easily handled and moved by the experimenter, technician or clinician. The complete apparatus of the present invention does require a base installation, or support unit 67, including relatively nonmobile elements, for power and gaseous sources, as will be described below. However, the hand manipulable unit as illustrated in FIG. 2 is very light, easy to operate, and can be readily extended and operated on any portion of the target organisms, even those which are relatively difficult to work with or noncooperative targets, such as large farm animals.

Figure 3:
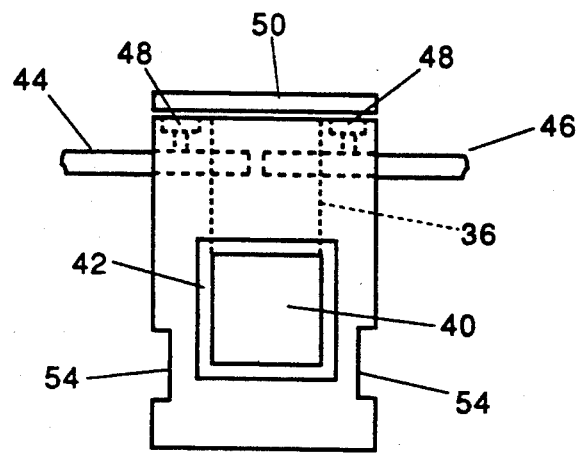
FIG. 3 is a side elevational view of the particle acceleration device of FIG. 2.
Figure 4:
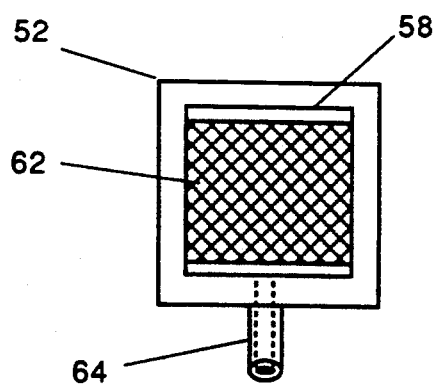
FIG. 4 is a front view and FIG. 5 is a side view of the retaining insert for use with the instrument of Figs. 2 and 3.

Turning to the details of the apparatus of FIGS. 2, 3 and 4, as shown in FIG. 2 the device includes a handle 30. The handle 30 is preferably elongated, and can be of any suitable shape or size adapted to the needs of the particular user of the instrument. As shown in FIG. 2, the handle 30 is merely an elongated bar. It is envisioned that in a more refined device, the handle could have more physiologically pleasing shape so as to be more adaptable for convenient use by a user. The handle is secured, as by screw 32, to an instrument body member 34.

The body member 34 has a hollowed out area in its interior, illustrated by the dash lines in FIGS. 2 and 3. This hollowed out internal area is a spark discharge chamber 36. The spark discharge chamber 36 is a largely rectangular opening extending to the upper edge of the body member 34, as may readily be viewed in FIGS. 2 and 3. The spark discharge chamber 36 is divided into upper and lower portions by a baffle 38, which extends rearwardly from the front edge of the spark discharge chamber 36, approximately midway vertically therein. At its lower edge, the spark discharge chamber 36 opens onto the front of the body member 34, through a discharge opening 40. At the discharge opening 40, there is further provided a recessed step 42, in the form of an enlarged opening of rectangular shape extending peripherally around the complete opening of the discharge port 40, and extending radially outward therefrom, recessed backwards from the front surface of the body member 34.

In the upper portion of the discharge chamber 36, extending inward from the lateral side edges of the body member 34, are a pair of electrodes 44 and 46. The electrodes 44 and 46 extend through the suitable apertures provided in the body member 34, into the interior of the spark discharge chamber 36, where their ends are spaced apart by the distance which forms the spark gap between the electrodes. Suitable countersunk set screws 48 are provided extending downwardly from the top of the body member 34 in bores provided for them, and are positioned so that set screws 48 will contact the respective electrodes 44 and 46. An end plate 50, consisting of a rectangular rigid sheet of material, is placed over the top of the body member 34 so as to close the top opening of the discharge chamber 36. The end plate 50 is preferably removably attached to the top of the body member 34, so that it can be removed for ready access to the interior of the spark chamber 36, and can be replaced in position closing the top of the discharge chamber 36.

A retaining screen holder unit 52 is a separate piece intended to interfit with the body member 34. The body member 34 has channels 54 cut into each of its two lateral sides. The channels 54 are L-shaped, having a long rearwardly extending lateral portion, and then a short upward leg at their rearward extent. Therefore, on the retaining screen holder unit 52, there is provided a pair of locking legs 56, which are corresponding in shape to the L-shaped channels 54 on the body member 34. The retaining screen unit 52 has a hollow bore 58 provided therethrough so that it is, in essence, a hollow box. Further it has provided in it a slot 60 provided in each of its lateral side edges, so that a retaining screen 62 can be inserted therethrough to extend completely across the front of the retaining screen unit 52, as can be seen in FIG. 4. At its bottom edge, the retaining screen unit 52 is provided with a gas port 64, which is provided with a gas fitting adapted suitable for attachment to conventional laboratory gas handling equipment. A flexible gas conduit 66 is attached to the gas port 64 at one end and to a reservoir of gaseous helium (not shown) at the other end. A pair of wires 68, one of which is shown in FIG. 2, connect the electrodes 46 and 48 to the base unit 67 of the apparatus. The gas conduit 66 and the wires 68 form an umbilical to connect the hand-held unit of FIG. 2 to the base unit 67.

Figure 5:
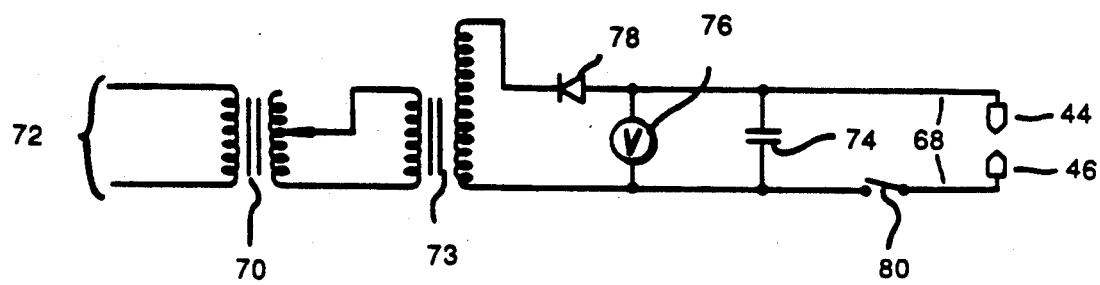

To further understand the apparatus of FIGS. 2 through 4, it is necessary to have a general idea how the power for the spark discharge electrodes is created. Shown in FIG. 5 is the basic electrical schematic diagram for the creation of the electric spark discharge which is supplied between the electrodes 44 and 46. It is to be understood that this is a basic electric schematic, omitting various interlocks and safety mechanisms of the type well known to those of ordinary skill in the art, but which is intended to illustrate generally how the electrical force for the device of FIGS. 2 through 5 is generated. A transformer 70 is connected to a conventional source of alternating current electrical power 72. The transformer 70 is preferably an auto transformer, which has a variable tap, so that the secondary voltage therefrom can be readily manually adjusted. The output of the auto transformer 70 is connected through a step-up transformer 73, which converts the voltage from the autotransformer 70 to extremely high electrical voltage. The output of the step-up transformer 73 is applied to a capacitor 74, which has a large storage capacity, preferably in the microfarad size range, and which is capable of withstanding voltages in a kilovolt range. A voltmeter 76 is provided to monitor the voltage applied to the capacitor 74, and a rectifying diode 78 assures that it is direct current voltage applied to the capacitor 74. A high voltage switch 80 is provided so as to close the connection between the capacitor 74 and the spark discharge electrodes 44 and 46.

The circuitry of FIG. 5, and a storage supply of helium gas, are located in a support unit to which the hand-held wand of FIGS. 2-4 is attached. The attachment is an umbilical cord for the wand and consists of the appropriate wires 68 to conduct the electrical voltage from the capacitor 72 to the electrodes 44 and 46 and a flexible conduit 66 for the helium gas. The umbilical is thus flexible, allowing extensive and easy freedom of movement of the hand-held unit of FIGS. 2 and 4 through the length of the umbilical connection.

Now the operation of the apparatus FIGS. 2 through 5 can be understood in detail. To operate the particle transformation apparatus, in addition to the apparatus shown in FIGS. 2 through 4, there must be a source of electric spark discharge voltage, such as that described by the circuit of FIG. 5. In addition, it is most advantageous if there is a source of gaseous helium. An electrical cable connects the spark discharge electrodes to the output of the voltage generation circuit of FIG. 5. In addition, a length of tubing can connect the gaseous source 62 to the source of gaseous helium. Thus the hand manipulable particle acceleration apparatus of FIGS. 2 through 5 is connected by the umbilical to a stationary source of supply, which includes both the electrical circuitry of FIG. 6 as well as the source of gaseous helium. To operate the apparatus of FIGS. 2 through 5, the end plate 50 is removed from the apparatus, and a droplet of water is placed between the ends of the spark discharge electrodes 46 and 44. If the spark discharge gap has changed in distance over time, due to variations in the device or wear in the electrodes, the gap between the electrodes can be adjusted readily by letting up on the set screws 48, and adjusting the electrodes before resetting the set screws. The gap between the electrodes should be approximately 2 millimeters. The electrodes themselves are simple cylinders of durable metallic material, such as steel.

Separately, and preferably previously, copies of the genetic material, either DNA or RNA, which is desired to be inserted into the target organism, have been coated onto carrier particles which are coated then in turn upon the carrier sheet of the type illustrated at 22 in FIG. 1. The carrier sheet for use within the present invention can be any stiff or semirigid sheet of light planar material, but is preferably saran-coated aluminized mylar. The carrier sheet is cut to a size so that it will fit within the recess step 42, provided in the front of the body member 34. To secure the carrier sheet in place, it is simply required that a light film of refrigerant oil be placed on the front facing face at the bottom of the step 42. Any low viscosity oil may be used for this purpose, such as alternatively a mineral oil. The oil will provide a light, but sufficient, adherence between the edge of the carrier sheet and the bottom of the step 42, so as to temporarily fix the carrier sheet in place. When the carrier sheet is in place, it covers the front of the discharge port 40. When that is done, the retaining screen unit 52 can be inserted into the front of the body member, and can be locked in place, by moving it upwardly with the legs 56 being retained in the L-shaped recesses 54. A helium flow can then be applied from the source of gaseous helium, through the input gas port 42.

Then the instrument is ready for use. The instrument can then be applied close to the living organism or tissue which is to be targeted. The front face of the carrier retaining screen 52 can be placed as close as a few millimeters from the surface of skin of the organism to be transformed. The switch 80 is then thrown, applying the high discharge electric voltage from the capacitor 72 through the electrodes 44 and 46. A spark discharge then jumps between the electrodes 44 and 46, instantly vaporizing the water droplet placed there between. The expanding shockwave reverberates throughout the shock chamber 34, but does not directly impact the carrier sheet, since it is protected by the baffle 38. However, the expanding shockwave then proceeds down the discharge chamber 36, to the lower half thereof, and proceeds out to the discharge port 40 with great force. The carrier sheet is lifted off of the retaining step 44, and hurled forwardly. The carrier sheet travels forwardly until it impacts the retaining screen 62 contained in the slot 60 in the front of the retaining screen unit 52. The carrier sheet impacts the retaining screen 62 and stops. The carrier particles fly off of the carrier sheet and proceed onwardly into the cells of the target organism. The carrier particles enter the cells of the organism. The genetic material on the carrier particles is thus introduced into the cells of the organism where the genetic material is, at a repeatable frequency, transiently expressed by the tissues of the target organism and, at a lesser but known statistical frequency, stably integrated into the gene element of the target cells. The target cells can be somatic cells of plant, animal or any other life form or, if germ line transformation is desired, can be germ line cells of the organism.

It has been found that the apparatus of FIGS. 2 through 5 is particularly convenient for the genetic transformation of the somatic cells of animals. For animals in general, and larger animals in particular, it is inconvenient to require that the animal be physically placed upon a stationary particle acceleration apparatus. The hand manipulable apparatus in FIGS. 2 through 5 can be readily placed on the surface of an animal, at any physical orientation, so that a particle-mediated genetic transformation procedure can be performed. It has further been found that the transformation procedure affected in this way is entirely painless. Through experimentation, it has been found that there is virtually no sensation to the target organism, other than a brief sensation of a breeze to the affected area. The impact and entry of the carrier particles is without physical sensation or pain to the target animal. Thus the apparatus appears ideally suited for application to human treatment, where somatic cell transformation is viewed as a potential route for treatment of genetic diseases.

The use of the helium facilitates the acceleration of the particles, by flushing the entire path of travel of the carrier sheet with helium, to replace the otherwise ambient atmospheric air. Helium is less dense than air. Accordingly, during the flight of the carrier sheet it encounters less resistance due to atmospheric drag. Therefore less motive force is required to accelerate the carrier sheet. Similarly, to the 44 and 46 to extent the helium flushes the area between the retaining screen 62 and the target organism, a similar affect is achieved with regard to the flight of the carrier particles alone. At the same time, since the helium is outside of the discharge chamber 36, which is sealed by the carrier sheet, the force applied to the carrier sheet is not diminished.

In this way, an easily hand manipulable particle acceleration devise is provided for the genetic transformation of organisms. It is the principal advantage of this device in that, although it is connected by an umbilical to a stationary source of supply, it can be readily manipulated in the aspect of the target animal. This has not been previously achievable in particle acceleration devices prior to design.

It is to be understood that the present invention is not limited to the particular embodiment disclosed herein but embraces all such modified forms thereof as come within the scope of the following invention.

We claim:

1. An apparatus for performing genetic transformation of a living organism in vivo by accelerating carrier particles coated onto a carrier sheet into the organism comprising a manually manipulable handle;

a body member mounted on the handle and of a size and shape so as to be readily carried and manually handled;

a carrier sheet;

the body member having an interior and a spark discharge chamber formed in the interior, the spark discharge chamber including a carrier sheet mounting location for mounting the carrier sheet thereon, the spark discharge chamber constructed so to present a shock wave to the carrier sheet mounting location;

a pair of electrodes extending into the body member and into the discharge chamber;

a carrier sheet retaining means removably attachable to the body member and located over the carrier sheet mounting location;

said carrier sheet retaining means including a retaining screen located spaced from the carrier sheet so that the carrier sheet will impact the retaining screen when accelerated from the carrier sheet mounting location;

a support unit including a source of electrical discharge energy; and an umbilical connecting the electrode to the support unit, so that electrical energy can be supplied to the electrodes for initiating an electric spark discharge between the electrodes while permitting the body member to be readily placed adjacent the organism to be transformed.

2. An apparatus as claimed in claim 1 wherein the body member has a front and the spark discharge chamber opens onto the front of the body member and wherein carrier sheet mounting location is a recessed step located surrounding an opening of the discharge chamber onto the front of the body member.

3. An apparatus as claimed in claim 1 wherein the carrier sheet retaining means includes a slot through which the retaining screen is inserted to be mounted in the carrier sheet retaining means.

4. An apparatus as claimed in claim 1 wherein the support unit includes a source of helium, wherein the carrier sheet retaining means includes an interior and a gas port through which gas may flow into the interior, and wherein the umbilical further includes means to conduct helium from the support unit to the gas port on the carrier sheet retaining means.

5. An apparatus as claimed in claim 1 wherein the body member includes ann opening into the discharge chamber adjacent to the electrodes and wherein there is further an end plate removably attached to the body member to cover the opening adjacent the electrodes so that convenient access can be had to the electrodes.

6. An apparatus for performing a genetic transformation of a living organism by the acceleration of carrier particles comprising:

a support unit constructed and arranged so as to supply a motive force for accelerating carrier particles into the organism; and hand-held means comprising a body member, a carrier sheet, and a retaining screen for retaining the carrier sheet attached to the body member, the body member having formed in it a discharge chamber constructed so as to generate a shock wave from said motive force and to direct shock wave therein toward the carrier sheet and constructed so as to hold the carrier sheet thereon in such a way that the shock wave will be applied to accelerate the carrier sheet, the retaining screen arranged so as to retain the carrier sheet after it is accelerated so that the carrier particles are separated therefrom; and umbilical means for transmitting the motive force from the support unit to the hand-held unit.

7. An apparatus as claimed in claim 6 wherein the motive force supplied by the support unit is electrical potential, and wherein the body member includes means therein to convert the electrical potential to physical force to accelerate the carrier sheet.

8. An apparatus as claimed in claim 7 wherein the means to convert the electrical force to physical force includes a pair of spaced electrodes which are bridged by a spark discharge when sufficient electrical potential is applied between them.

9. An apparatus as claimed in claim 6 wherein the support unit further includes a source of helium, wherein the umbilical means further includes means to conduct the helium to the hand-held unit, and wherein the hand-held unit further includes means to conduct the helium to the path of travel of the carrier sheet.

10. An apparatus as claimed in claim 6 wherein the retaining screen is removably attached to the body member so that the carrier sheet may be placed in the body member.

* * * * *